United States Patent
Douglas

(10) Patent No.: US 11,790,618 B1
(45) Date of Patent: *Oct. 17, 2023

(54) ENHANCED 3D TRAINING ENVIRONMENT

(71) Applicant: Robert Edwin Douglas, Winter Park, FL (US)

(72) Inventor: Robert Edwin Douglas, Winter Park, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/744,715

(22) Filed: May 15, 2022

Related U.S. Application Data

(63) Continuation-in-part of application No. 17/334,867, filed on May 31, 2021, now Pat. No. 11,341,731, which is a continuation-in-part of application No. 17/187,828, filed on Feb. 28, 2021, now abandoned, which is a continuation of application No. 17/120,109, filed on Dec. 12, 2020, now Pat. No. 10,973,485, which is a continuation of application No. 16/594,139, filed on Oct. 7, 2019, now Pat. No. 10,893,844, which is a continuation-in-part of application No. 15/949,202, filed on Apr. 10, 2018.

(60) Provisional application No. 62/743,837, filed on Oct. 10, 2018.

(51) Int. Cl.
| | |
|---|---|
| *G06T 19/00* | (2011.01) |
| *A61B 6/00* | (2006.01) |
| *A61B 6/02* | (2006.01) |
| *A61B 90/00* | (2016.01) |
| *G06T 7/00* | (2017.01) |
| *G06T 15/08* | (2011.01) |
| *G02B 27/01* | (2006.01) |
| *G06T 11/60* | (2006.01) |

(52) U.S. Cl.
CPC ............ *G06T 19/006* (2013.01); *A61B 6/025* (2013.01); *A61B 6/502* (2013.01); *A61B 6/5211* (2013.01); *A61B 90/39* (2016.02); *G02B 27/017* (2013.01); *G06T 7/0014* (2013.01); *G06T 11/60* (2013.01); *G06T 15/08* (2013.01); *A61B 2090/3904* (2016.02); *G06T 2207/10112* (2013.01); *G06T 2207/10124* (2013.01); *G06T 2207/20036* (2013.01); *G06T 2207/30068* (2013.01)

(58) Field of Classification Search
None
See application file for complete search history.

(56) References Cited

U.S. PATENT DOCUMENTS

| | | | |
|---|---|---|---|
| 8,791,857 B2* | 7/2014 | Mo .................... | G01S 19/11 342/357.48 |
| 2006/0208946 A1* | 9/2006 | Bailey ................. | G01S 19/11 342/386 |
| 2012/0166146 A1* | 6/2012 | Cincotti .............. | F41H 3/00 703/1 |
| 2012/0286992 A1* | 11/2012 | Tekin .................. | H01Q 1/007 342/357.48 |
| 2014/0180451 A1* | 6/2014 | Marty ................. | G06F 3/016 700/91 |
| 2016/0165220 A1* | 6/2016 | Fujimaki ............ | G09G 3/001 345/87 |

(Continued)

*Primary Examiner* — Jwalant Amin

(57) ABSTRACT

A method for immersively displaying a scanned environment of a region to a set of users in a training environment wearing augmented reality head display units. The training environment includes a pseudo-GPS system, which allows position tracking over time. This enables rehearsing military operations before they occur.

19 Claims, 14 Drawing Sheets

(56) References Cited

U.S. PATENT DOCUMENTS

| | | | |
|---|---|---|---|
| 2016/0187652 A1* | 6/2016 | Fujimaki | G02B 27/0172 345/8 |
| 2016/0187661 A1* | 6/2016 | Yajima | G02B 27/0172 345/8 |
| 2018/0059250 A1* | 3/2018 | Nakata | G01S 19/396 |

* cited by examiner

WAREHOUSE WITH PSEUDO-GPS AND IMPORTED FOREIGN TERRAIN

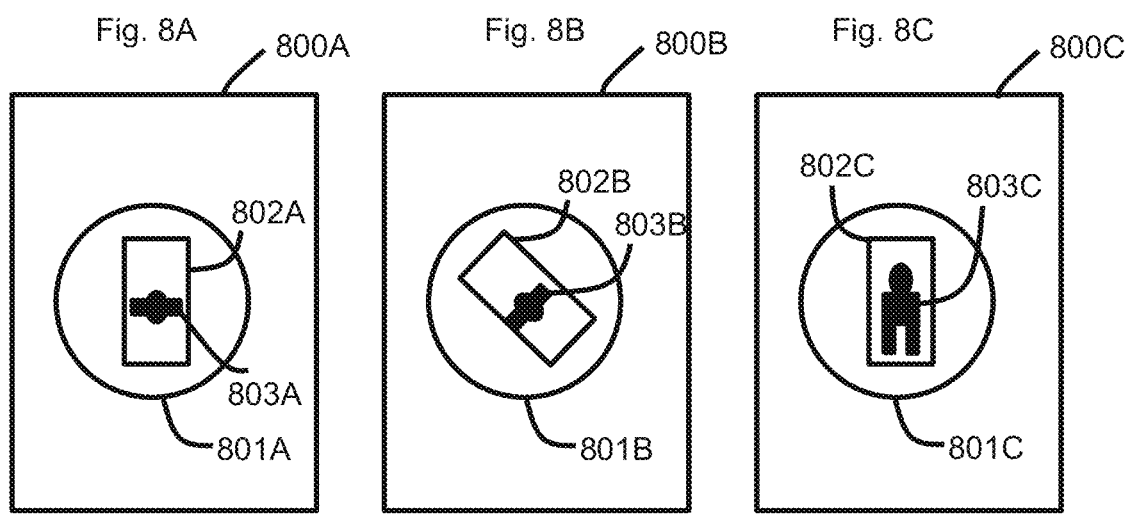

PSEUDO-GPS SYSTEM

| Time (in seconds) | Unit involved | Example time received by soldier #1's equipment | Example time received by soldier #N's equipment |
|---|---|---|---|
| 1 | 1 pings | 1.5 | 1.9 |
| 2 | 2 pings | 2.6 | 2.1 |
| 3 | 3 pings | 3.7 | 3.1 |
| 4 | 1 pings | 4.55 | 4.9 |
| 5 | 2 pings | 5.66 | 5.1 |
| 6 | 3 pings | 6.8 | 6.1 |

EXAMPLES OF AREAS AND REGIONS

| Example | Region scanned by LIDAR | Area where pseudo-GPS system is set up |
|---|---|---|
| Example 1 | Kabul | Warehouse |
| Example 2 | Bagram | Field at Ft. Benning |
| Example 3 | Hyde Park | Backyard at a home |
| Example 4 | Taj Mahal | Family room at a home |
| Example 5 | Museum | Office at a home |

ENHANCED 3D TRAINING ENVIRONMENT

CROSS-REFERENCES TO RELATED APPLICATIONS

The present application is a continuation in part of U.S. patent application Ser. No. 17/334,867 filed on May 31, 2021, which is a continuation in part of U.S. patent application Ser. No. 17/187,828 filed on Feb. 28, 2021, which is a continuation of U.S. patent application Ser. No. 17/120,109 filed on Dec. 12, 2020, which is a continuation of U.S. patent application Ser. No. 16/594,139 filed on Oct. 7, 2019, which claims the benefit of U.S. Provisional Application 62/743,837 filed on Oct. 10, 2018. U.S. patent application Ser. No. 17/334,867 is also a continuation-in-part of U.S. patent application Ser. No. 15/949,202 filed on Apr. 10, 2018.

TECHNICAL FIELD

Aspects of this disclosure are generally related to 3D imaging.

BACKGROUND

Augmented reality head display units have capability to simultaneously display real world objects as well as the virtual world.

SUMMARY

All examples, aspects and features mentioned in this document can be combined in any technically possible way.

This patent discloses hardware, software and methods. Some embodiments comprise selecting a dataset of a region wherein said dataset comprises a LIDAR scan of a region. For example, a region of terrain in Afghanistan. Additionally, register the dataset of said region to a specific area, such as a warehouse. Additionally, implement a transceiver system in said area. Additionally, receive at a first time point, by an augmented reality head display unit (HDU) a first signal from said transceiver system wherein said HDU is located in said area. Additionally, process said first signal, by a processor in communication with said HDU, to compute a first location of said HDU. Additionally, generating a first image set of said region wherein said first image set comprises a first left eye image and a first right eye image wherein said first left eye image is generated based on at least a first left eye viewpoint, a first left eye viewing angle and said dataset of said region, wherein said first right eye image is generated based on at least a first right eye viewpoint, a first right eye viewing angle and said dataset of said region. Additionally, display said first image set on said HDU wherein said first left eye image is aligned with a left eye of a user and said first right eye image is aligned with a right eye of said user. Additionally, receive at a subsequent time point, by said HDU a subsequent signal from said transceiver system wherein said HDU is located in said area. Additionally, process said subsequent signal, by said processor in communication with said HDU, to compute a subsequent location of said HDU wherein said subsequent location is different from said first location. Additionally, generate a subsequent image set of said region wherein said subsequent image set comprises a subsequent left eye image and a subsequent right eye image wherein said subsequent left eye image is generated based on at least a subsequent left eye viewpoint, a subsequent left eye viewing angle and said dataset of said region, wherein said subsequent left eye viewpoint is different from said first left eye viewpoint, wherein said subsequent left eye viewing angle is different from said first left eye viewing angle, wherein said subsequent right eye image is generated based on at least a subsequent right eye viewpoint, a subsequent right eye viewing angle and said dataset of said region, wherein said subsequent right eye viewpoint is different from said first right eye viewpoint, wherein said subsequent left eye viewing angle is different from said right left eye viewing angle. Additionally, displaying said subsequent image set on said HDU wherein said subsequent left eye image is aligned with said left eye of said user and said subsequent right eye image is aligned with said right eye of said user.

Some embodiments comprise wherein said region is the same as said area. The region would therefore be superimposed on the area. It should be noted that in some embodiments, the time points may be real time. In other embodiments, the time points could be temporally separated. For example, the dataset of the region could be from 2020 and the user could be viewing the region in 2021.

Some embodiments comprise wherein said region is different from said area. For example, the region scanned with LIDAR could be of Afghanistan. The area where the dataset is used could be a warehouse in Texas.

Some embodiments comprise wherein said HDU displays a location derived from a positioning system of said region. Some embodiments comprise wherein said positioning system comprises at least one of the group consisting of: a global positioning system (GPS); a nominal positioning system (NPS); and a map and compass.

Some embodiments comprise wherein an element of said HDU comprises an inertial measurement unit (IMU) wherein head tracking capabilities are enabled.

Some embodiments comprise wherein said region comprises one of the group consisting of: a battlefield; a forest fire; and a hurricane damaged region.

Some embodiments comprise wherein said area comprises one of the group of:

a warehouse; a room; and, a field. Some embodiments comprise wherein said warehouse area contains a transportation system, which could be in communication with said positioning system. Transportation systems could include treadmills (e.g., standard or omni-directional) or stationary cars (which simulate movement).

Some embodiments comprise wherein multiple additional users in said area wear HDUs and view 3D imagery of said region. Some embodiments comprise wherein said area can contains at least two of the group consisting of: a friendly forces group; a neutral forces group; and an adversarial forces group.

Some embodiments comprise wherein said area contains barrier(s) wherein said barrier(s) does not block intervisibility amidst members of a single group, and wherein said barrier(s) may block intervisibility amidst members of different groups.

Some embodiments comprise wherein said user and said multiple additional users carry equipment that can also be located via the positioning system.

Some embodiments comprise wherein said friendly forces group and said adversarial forces group interact with one another such that virtual damage could be inflicted by the friendly forces group on the adversarial forces group and by the adversarial forces group on the friendly forces group. Some embodiments comprise wherein data from an interaction of said friendly forces group and said adversarial forced group is recorded. Some embodiments comprise wherein said recorded data can be summarized for subsequent analysis or education purposes. Some embodiments comprise wherein a virtual adversarial group is presented on HDU's of said friendly forces group; and wherein a virtual friendly forces group is presented on HDU's of said adversarial forces group.

Some embodiments comprise wherein said LIDAR is at least one of the group consisting of: aircraft-based LIDAR; space-based LIDAR; water-based LIDAR; and ground-based LIDAR.

Some embodiments comprise wherein at least one additional user wearing HDU(s) is located in at least one additional area and views 3D imagery of said region wherein said at least one additional area is different from said specific area.

In this patent, a region can be defined as any volume, such as terrain, building(s), city(ies), space, underwater environments. For example, a region could be a part of a country or the world having definable characteristics, but now always fixed boundaries. In this patent, the LIDAR scan is of the region. A nominal positioning system (NPS) that mirrors the capabilities of GPS that generates data based on a specific area without linkage to the GPS constellation ephemeris data.

It is important to display accurate geometric rendering on the head display unit to provide a realistic view. For example, consider the following. Some of the virtual objects could be zoomed with a picture-in-picture like display.

| Distance (in feet) | 100 | 1000 | 5000 |
|---|---|---|---|
| Tree height (in feet) | 30 | 30 | 30 |
| Height of glasses (in feet) | 5 | 5 | 5 |
| Net height (in feet) | 25 | 25 | 25 |
| Look up angle to top of tree (in degrees) | 14.03 | 1.43 | 0.29 |
| Look down angle toward person's shoes (in degrees) | 2.86 | 0.29 | 0.06 |

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides steps explained herein that when performed (e.g. when executing) on the processor, operates as explained herein within the computerized device to perform all of the method embodiments and operations explained herein as embodiments of the invention. Thus any computerized device that performs or is programmed to perform processing explained herein is an embodiment of the invention.

Other arrangements of embodiments of the invention that are disclosed herein include Software programs to perform the method embodiment steps and operations Summarized above and disclosed in detail below. More particularly, a computer program product is one embodiment that has a computer-readable medium including computer program logic encoded thereon that when performed in a computerized device provides associated operations providing steps as explained herein.

The computer program logic, when executed on at least one processor with a computing system, causes the processor to perform the operations (e.g., the methods) indicated herein as embodiments of the invention. Such arrangements of the invention are typically provided as Software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other Such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as Software and hardware, or as hardware and/or circuitry alone. Such as within a data communications device. The features of the invention, as explained herein, may be employed in data processing devices and/or Software systems for Such devices. Note that each of the different features, techniques, configurations, etc. discussed in this disclosure can be executed independently or in combination. Accordingly, the present invention can be embodied and viewed in many different ways. Also, note that this Summary section herein does not specify every embodiment and/or incrementally novel aspect of the present disclosure or claimed invention. Instead, this Summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF FIGURES

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 8A illustrates a design with a first area, such as a room in Florida.

FIG. 8B illustrates a design with a second area, such as a room in Texas.

FIG. 8C illustrates a design with a third area, such as a room in California.

FIG. 10 illustrates example regions and associated areas.

DETAILED DESCRIPTION OF FIGURES

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1:
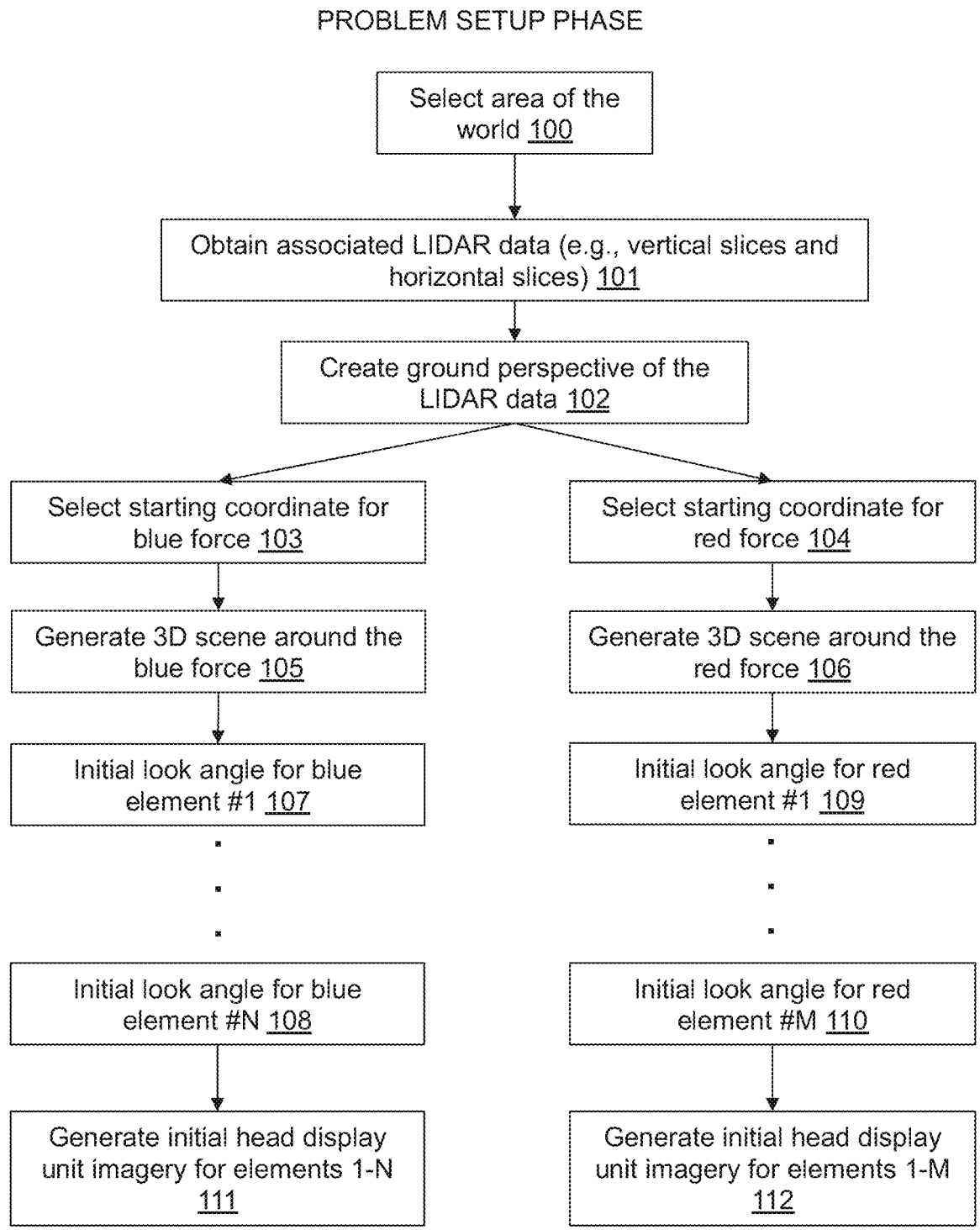
FIG. 1 illustrates the problem setup phase.

FIG. 1 illustrates the problem setup phase. 100 illustrates selecting an area of the world. For example, an area selected could be Kabul, Afghansitan. 101 illustrates obtaining associated light detection and ranging (LIDAR) data. This can be in the form of airborne LIDAR acquired from aircraft flying overhead or from ground based lidar acquisition. The datasets would be 3-dimensional, such as horizontal and vertical slices per Anderson, K., Hancock, S., Casalegno, S., Griffiths, A., Griffiths, D., Sargent, F., McCallum, J., Cox, D. T. C. and Gaston, K. J., 2018. Visualising the urban green volume: Exploring LiDAR voxels with tangible technologies and virtual models. *Landscape and Urban Planning*, 178, pp. 248-260. 102 illustrates creating the ground perspective of the LIDAR data, such as is performed using methods disclosed in U.S. Pat. No. 8,384,771. At this juncture, the buildings and trees and different mountains would be evident to a ground observer wearing a head display unit, such as the integrated visual augmentation system (IVAS). 103 illustrates selecting a starting coordinate for blue force. A blue force is a term that is used typically for the United States force element. The exercise would typically commence from the starting point and be oriented on the location of a red or opposing force provided by the blue force intelligence. 104 illustrates selecting a starting coordinate for red force. A red force is a term that is used typically for the enemy force element. This need not coincide with the location provided by blue force intelligence. 105 illustrates generating a 3D scene around the blue force. 106 illustrates generating a 3D scene around the red force. 107 illustrates an initial look angle for blue force element #1. This process is continued for the various members of the blue force. 108 illustrates an initial look angle for blue force element #N. 109 illustrates an initial look angle for red force element #1. This process is continued for the various members of the red force. 110 illustrates an initial look angle for red force element #M. 111 illustrates generating an initial head display unit imagery for elements 1-N. 112 illustrates generating an initial head display unit imagery for elements 1-M. At this juncture, both the red and the blue force have been initialized and are ready to commence the exercise.

Figure 2:
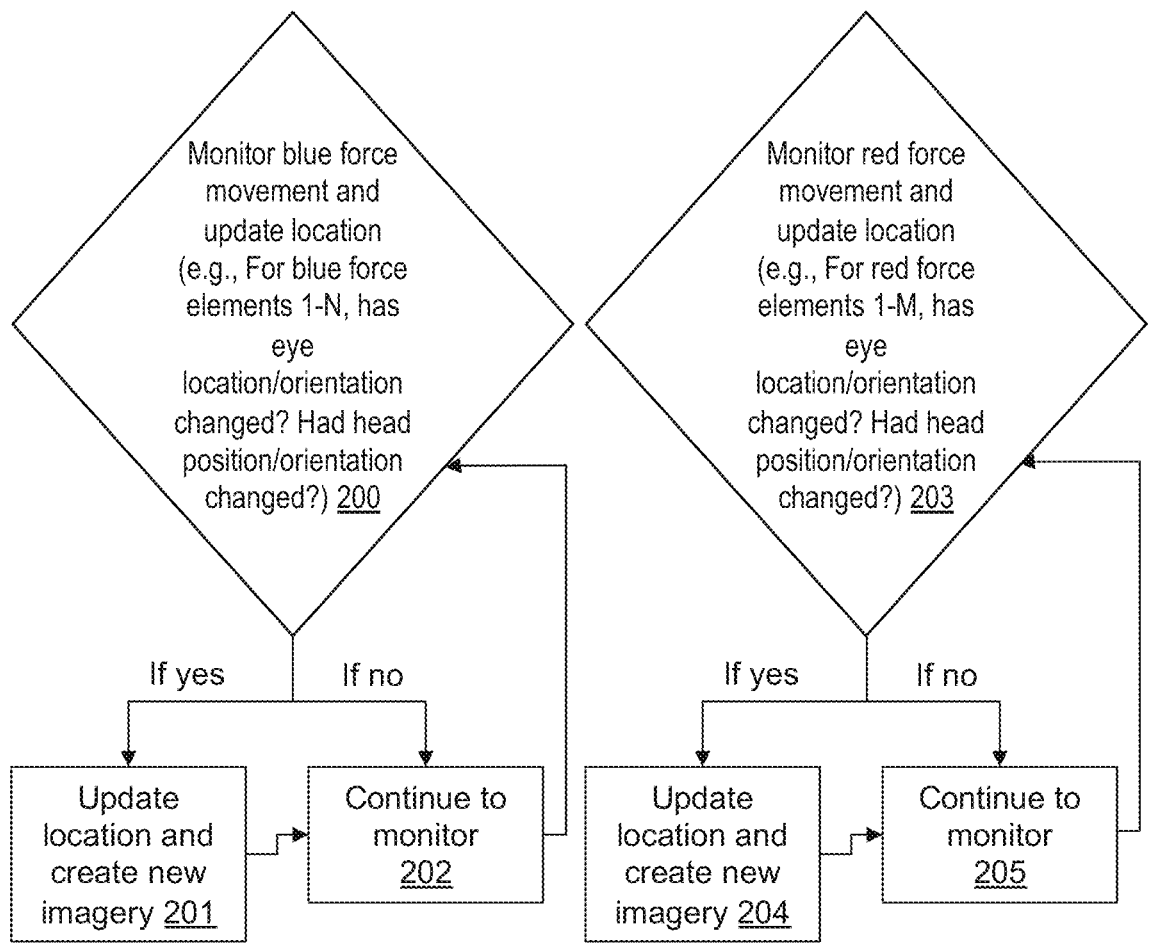
FIG. 2 illustrates movement dynamics for the blue and red forces.

FIG. 2 illustrates movement dynamics for the blue and red forces. This figure illustrates the movement of elements over multiple time sequential time periods. 200 illustrates monitoring blue force movement and updating location. For blue force elements 1-N, has eye location/orientation changed? Had head position/orientation changed? If yes, move to processing block 201. If no, move to processing block 202. At processing block 201, the location of each of the elements would be updated and any changes in the look angles or eye positions would be updated. At this point, a new set of imagery would be created for each of the elements that had changes in these locations or look angles. An example would be that blue force element 3 change his viewing angle from looking North to looking Northeast. After completion of 201, then the move to processing block 202. At processing block, 202, then move to processing block 200. An example would be that blue force element 7 had an unchanged head position/orientation and unchanged eye position/orientation over this time period. For example, blue force element 7 looked North over the entire time period. 203 illustrates monitoring red force movement and updating location. For red force elements 1-M, has eye location/orientation changed? Had head position/orientation changed? If yes, move to processing block 204. If no, move to processing block 205. At processing block 204, the location of each of the elements would be updated and any changes in the look angles or eye positions would be updated. At this point, a new set of imagery would be created for each of the elements that had changes in these locations or look angles. An example would be that red force element 9 change his viewing angle from looking South to looking Southwest. After completion of 204, then the move to processing block 205. At processing block, 205, then move to processing block 203. An example would be that red force element 11 had an unchanged head position/orientation and unchanged eye position/orientation over this time period. For example, red force element 11 looked South over the entire time period.

Figure 3:
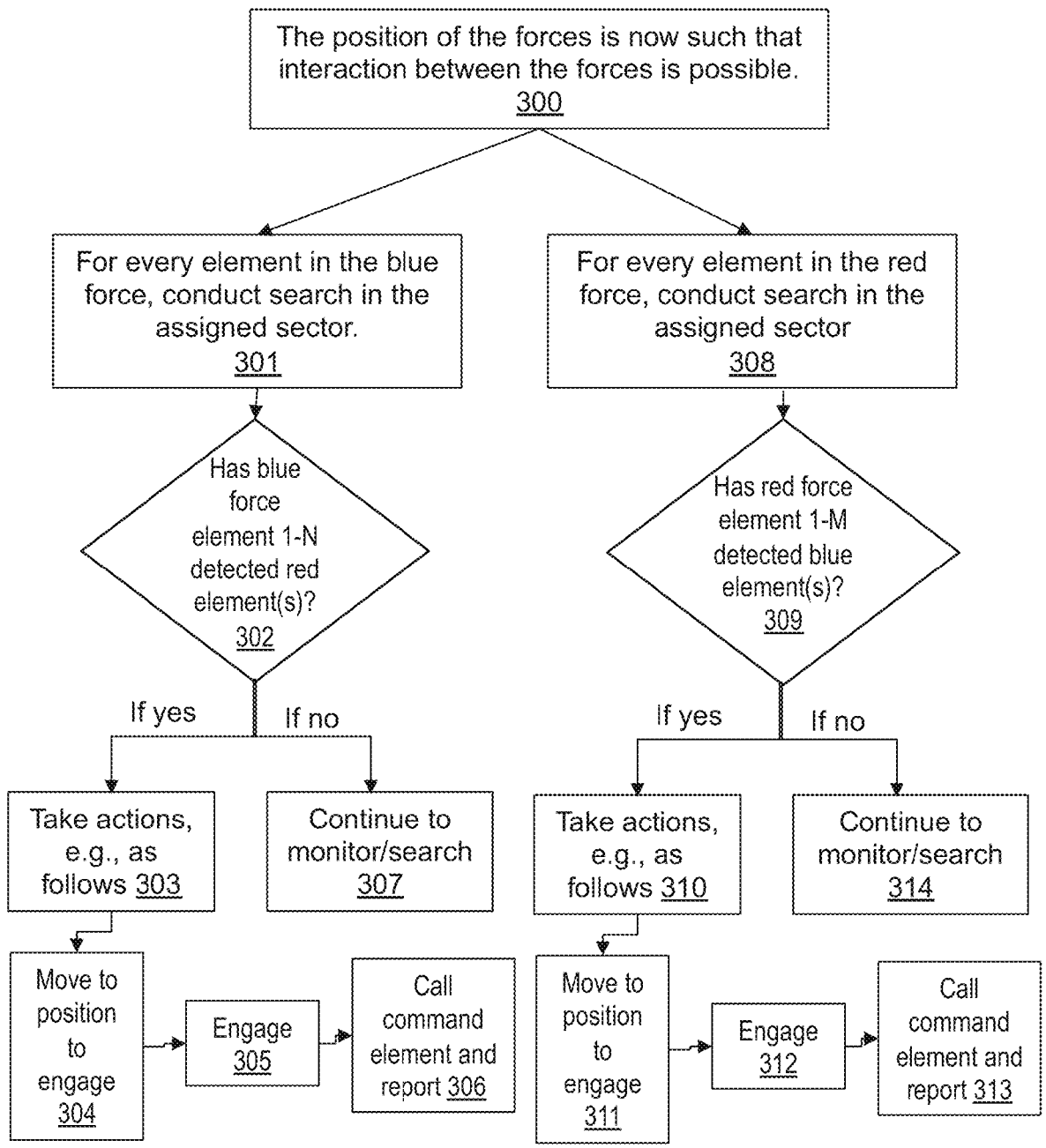
FIG. 3 illustrates example action dynamics.

FIG. 3 illustrates example action dynamics. 300 illustrates wherein the position of the forces is now such that interaction between the forces is possible. 301 illustrates wherein for every element in the blue force, conduct search in the assigned sector. 302 illustrates the decision point of whether blue force element 1-N detected red element(s)? If yes, move to 303. If for example, if blue force element #4 has detected a red element, he/she determines to take actions as follows. 304 illustrates wherein a blue force moves to a position to engage (e.g., behind a rock). 305 illustrates engagement, such as firing a weapon. These actions would typically be coordinated and directed by the blue unit leader. 306 illustrates calling the command element and reporting the actions. If the answer to 302 is no, then move to 307. 307 illustrates continuing to monitor/search. 308 illustrates wherein for every element in the red force, conduct search in the assigned sector. 309 illustrates the decision point of whether red force element 1-M detected blue element(s)? If yes, move to 310. If for example, if red force element #19 has detected a blue element, he/she determines to take actions as follows. 311 illustrates wherein a red force moves to a position to engage (e.g., behind a tree). 312 illustrates engagement, such as firing a weapon. These actions would typically be coordinated and directed by the red unit leader. 313 illustrates calling the command element and reporting the actions. If the answer to 309 is no, then move to 314. 314 illustrates continuing to monitor/search.

Figure 4:
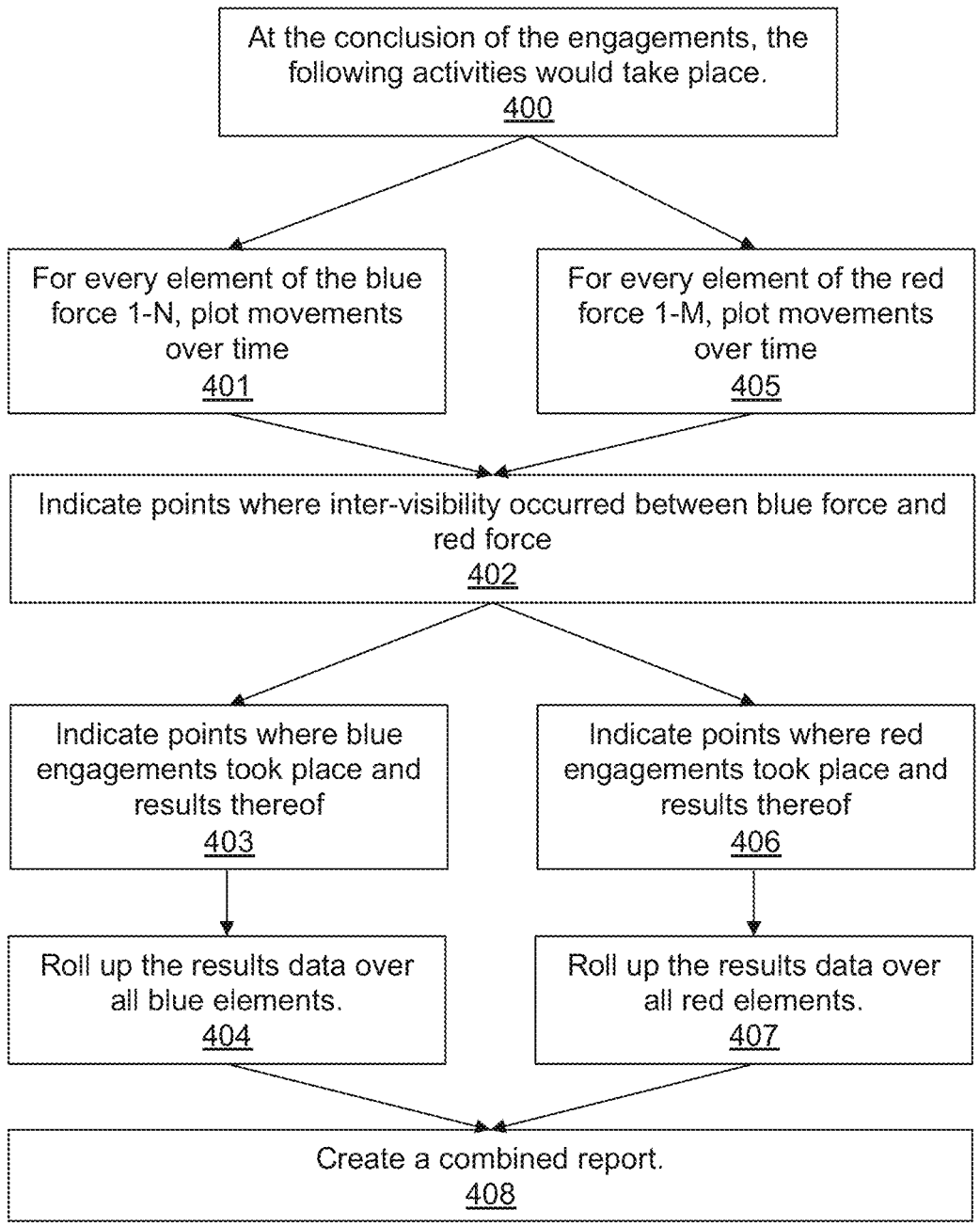
FIG. 4 illustrates example after action activities.

FIG. 4 illustrates example after action activities. 400 illustrates at the conclusion of the engagements, the following example activities would take place. Note that during the course of the initial setup to the conclusion of the exercise, there would be continuous recording of all elements' locations, orientations and activities over the duration of the exercise. 401 illustrates for every element of the blue force 1-N, plot movements over time. 402 illustrates indicating points where inter-visibility occurred between blue force and red force. 403 illustrates indicating points where blue engagements took place and results thereof. 404 illustrates rolling up the results data over all blue elements. 405 illustrates for every element of the red force 1-M, plot movements over time. 406 illustrates indicating points where red engagements took place and results thereof. 407 illustrates rolling up the results data over all red elements. 408 illustrates creating a combined report.

Figure 5:
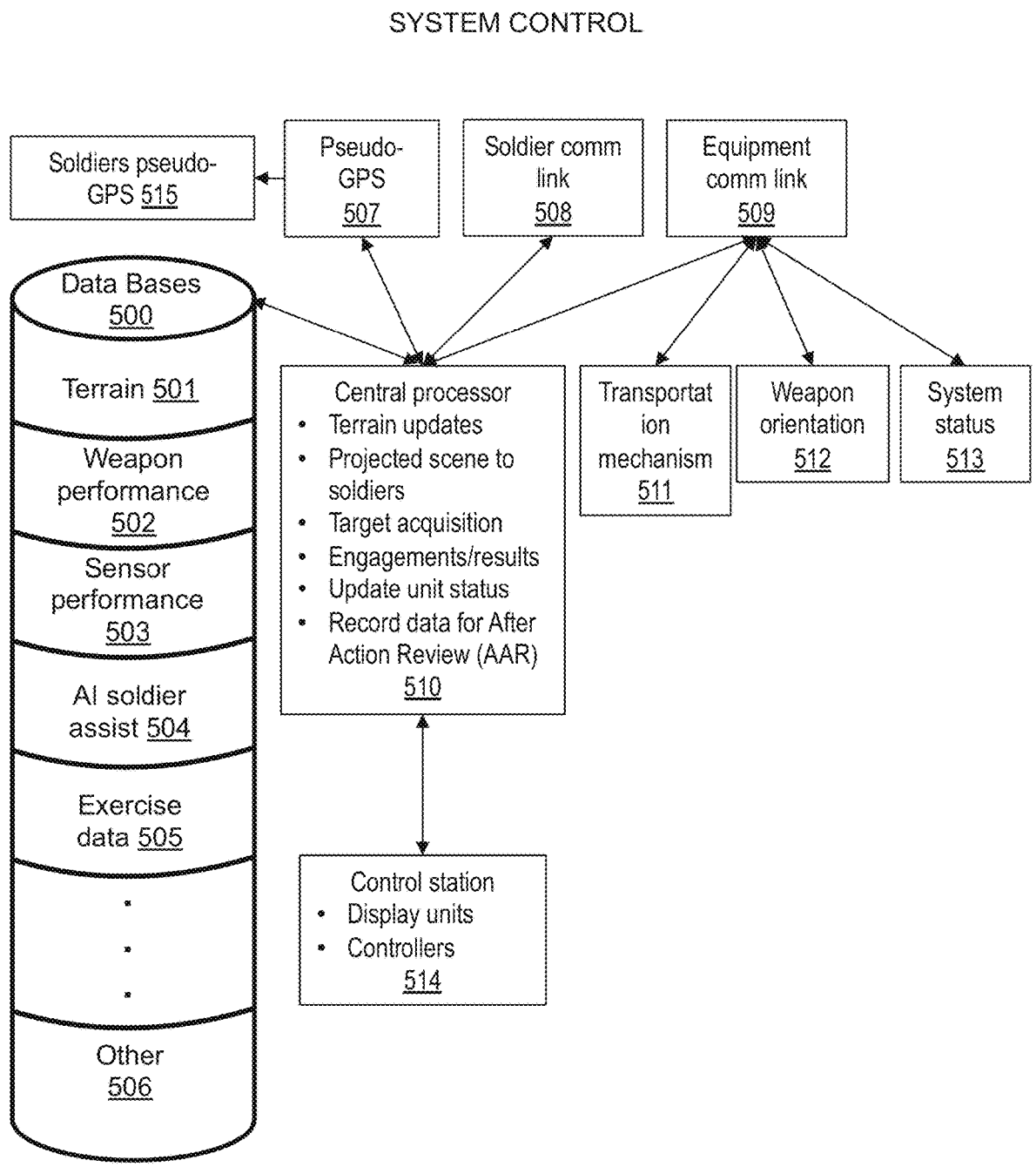
FIG. 5 illustrates the system control.

FIG. 5 illustrates the system control. 500 illustrates a set of interrelated databases. 501 illustrates a terrain database. A 3D volume cursor, as taught in U.S. Pat. No. 9,980,691 can be used to select a region of interest from a large volume. 502 illustrates a weapons performance database (range, accuracy, penetration, etc.). 503 illustrates a sensor performance database (NE ΔT). 504 illustrates an AI soldier assist database. 505 illustrates an exercise database. 506 illustrates other databases, as needed for a particular exercise. 507 illustrates the pseudo-GPS system. 508 illustrates the soldier communication link. 509 illustrates the equipment communication link. 510 illustrates the central processor, which provides terrain updates, a projected scene to soldiers, target acquisition, engagements and results thereof, updates on unit status and records data for after action reviews (AAR). 511 illustrates a transportation mechanism (e.g., virtual treadmill, virtual car, etc.), which are an option for the warehouse concept. 512 illustrates a weapon orientation. 513 illustrates a system status. 514 illustrates a control station. 515 illustrates soldier's pseudo-GPS system. Nominally, the soldier's pseudo-GPS position would be updated as a result of movements (direction and speed and duration) of the transportation mechanism over time. In the event, however, the soldier departed the transportation mechanism, the soldier's position could be computed and the equipment must have an inertial measurement unit (IMU), which could communicate changes in location of the soldier through the GPS system and onto the central processing unit.

Figure 6:
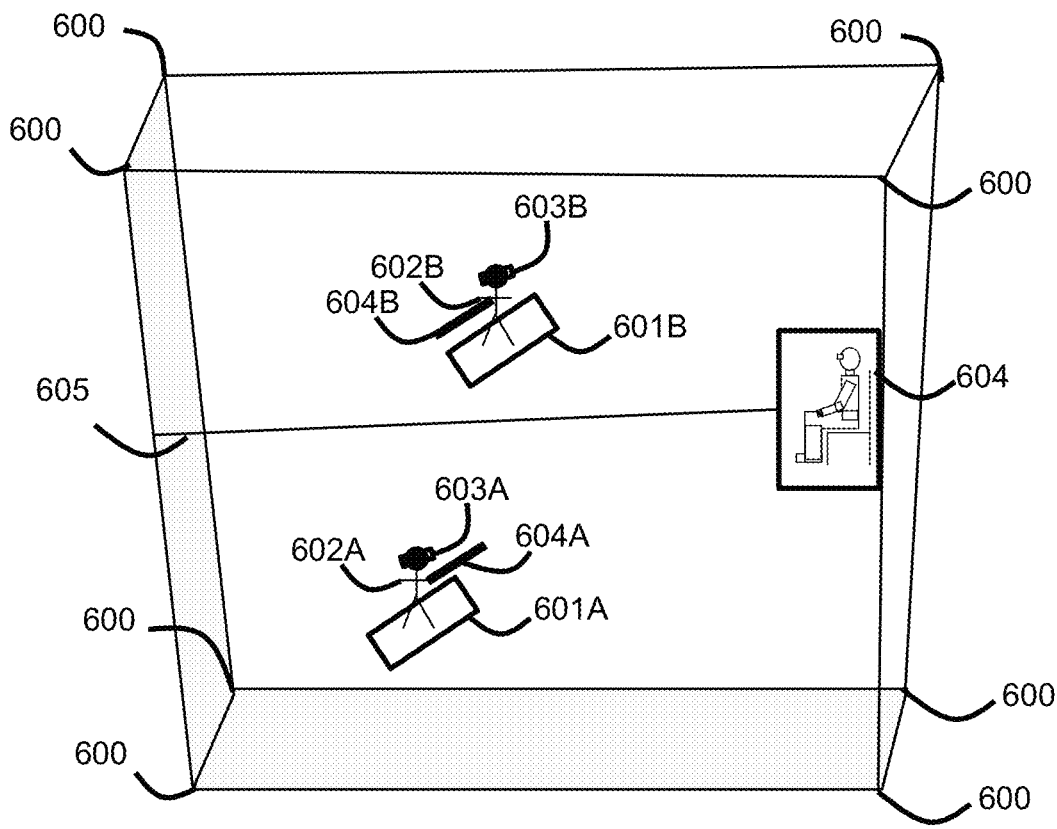
FIG. 6 illustrates the interior of a warehouse with a pseudo-GPS and an imported foreign terrain.

FIG. 6 illustrates the interior of a warehouse with a pseudo-GPS and an imported foreign terrain. It is the goal is to perform accurate geometric rendering of imagery associated with the location and orientation of the HDUs. 600 illustrates transceivers, which in the preferred embodiment are placed in the corners of the warehouse. 601A illustrates a treadmill for the blue soldier. It should be noted that the incline of the treadmill can be adjusted to match the slope of the terrain. 602A illustrates a blue soldier. Although a single soldier is depicted, there would, in fact be N such soldiers. 603A illustrates an augmented reality headset, such as the IVAS worn by the blue soldier 602A. 604A illustrates a training rifle carried by the blue soldier 602A. 601B illustrates a treadmill for the red soldier. 602B illustrates a red soldier. Although aa single soldier is depicted, there would, in fact, be M red soldiers present. 603B illustrates an augmented reality headset, such as the IVAS worn by the red soldier 602B. 604B illustrates a training rifle carried by the red soldier 602B. 605 illustrates a barrier, which is an optional element of the overall system. Note that multiple squad mates could be in the same room. Note that the area could be an open field. Note that the existing space-based GPS system could be used to track the location of users and this could be converted to the region's GPS. Note that having a low ratio of transceivers to users would be cost effective.

Figure 7:
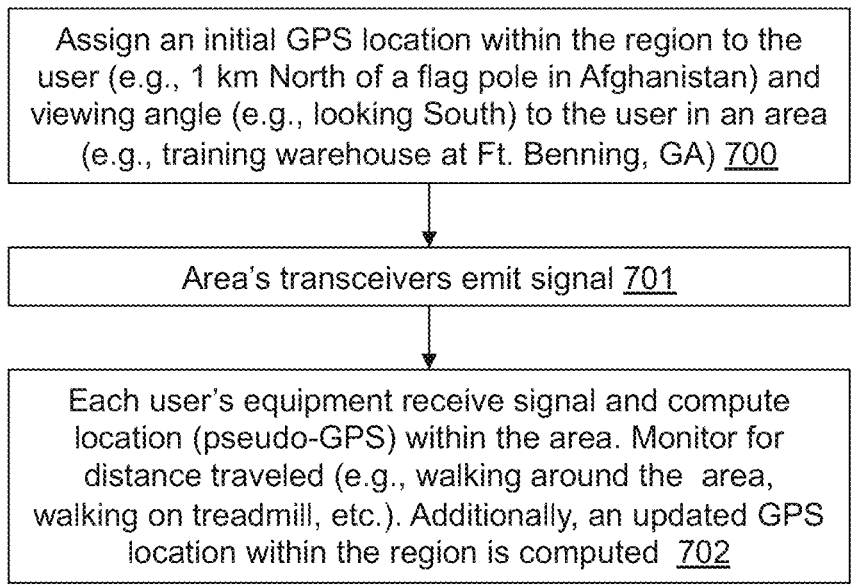
FIG. 7 illustrates determining a user's coordinate in the virtual world.

FIG. 7 illustrates determining a user's coordinate in the virtual world. 700 illustrates assigning an initial GPS location within the region to the user (e.g., 1 km North of a flag pole in Afghanistan) and viewing angle (e.g., looking South) to the user in an area (e.g., training warehouse at Ft. Benning, Ga.). 701 illustrates wherein the area's transceivers emit a signal. 702 illustrates wherein each user's equipment receive signal and compute location (pseudo-GPS) within the area. Monitor for distance traveled (e.g., walking around the area, walking on treadmill, etc.). Additionally, an updated GPS location within the region is computed. For example, assume a user's initial GPS location is at a building located at 1 km North of a flag pole in Afghanistan. Assume that a user is facing South. The use will initially see in the virtual world in the augmented reality/mixed reality headset, the surroundings at the building. Assume that the treadmill is activated and the user is walking at 2 km/hour on the treadmill oriented Southward in the virtual world, the virtual world displayed on the user's HDU would be slowly changing from the initial building and at approximately 30 minutes, the user would arrive at the virtual flagpole. For example, assume that a user steps off of the treadmill and now wanders around the warehouse. The use would then be able to walk around the room and see the virtual scene surrounding the flagpole.

FIG. 8A illustrates a design with a first area, such as a room in Florida. 800A illustrates the first area, which is equipped with a set of transceivers. 801A illustrates a platform, which in the preferred embodiment has is on a swivel. 802A illustrates a treadmill, which has adjustable incline angle. An omni-directional treadmill (e.g., ball bearings design) could be used in combination with an adjustable angle platform could be used. This could be linked to the GPS location of the region (e.g., Afghanistan), such that the slope of the treadmill could match the slope of the region. 803A illustrates a first user. Note that the first user would have a first pseudo-GPS location (within the area) and an associated GPS location (within the room could be calculated). For example, this first user's would have GPS location at 1.0 km South of a flag pole in Afghanistan, facing North and walking in the North direction.

FIG. 8B illustrates a design with a second area, such as a room in Texas. 800B illustrates the second area, which is equipped with a set of transceivers. 801B illustrates a platform, which in the preferred embodiment has is on a swivel. 802B illustrates a treadmill, which has adjustable incline angle. An omni-directional treadmill (e.g., ball bearings design) could be used in combination with an adjustable angle platform could be used. This could be linked to the GPS location of the region (e.g., Afghanistan), such that the slope of the treadmill could match the slope of the region. 803B illustrates a second user. Note that the first user would have a first pseudo-GPS location (within the area) and an associated GPS location (within the room could be calculated). For example, this second user's would have GPS location at 1.1 km South of a flag pole in Afghanistan, facing Northwest and walking in the Northwest direction.

FIG. 8C illustrates a design with a first area, such as a room in California. 800C illustrates the third area, which is equipped with a set of transceivers. 801C illustrates a platform, which in the preferred embodiment has is on a swivel. 802C illustrates a treadmill, which has adjustable incline angle. An omni-directional treadmill (e.g., ball bearings design) could be used in combination with an adjustable angle platform could be used. This could be linked to the GPS location of the region (e.g., Afghanistan), such that the slope of the treadmill could match the slope of the region. 803C illustrates a third user. Note that the first user would have a first pseudo-GPS location (within the area) and an associated GPS location (within the room could be calculated). For example, this third user's would have GPS location at 0.8 km South of a flag pole in Afghanistan, facing North and low crawling in the North direction.

Figures 9A, 9B:
FIG. 9A illustrates three transceivers used in the pseudo-GPS system for the area.
FIG. 9B illustrates signal received by a moving soldier and a stationary soldier.

FIG. 9A illustrates three transceivers used in the pseudo-GPS system for the area. Transceiver #1, Transceiver #2 and Transceiver #3 are illustrated. Note that these are placed in the area.

FIG. 9B illustrates signal received by a moving soldier and a stationary soldier. At time=1 second, Transceiver #1 pings and the ping from Transceiver #1 is received by soldier #1's equipment at 1.5 seconds and soldier #2's equipment at 1.9 seconds. At time=2 seconds, Transceiver #2 pings and the ping from Transceiver #2 is received by soldier #1's equipment at 2.6 seconds and soldier #2's equipment at 2.1 seconds. At time=3 second, Transceiver #3 pings and the ping from Transceiver #3 is received by soldier #1's equipment at 3.7 seconds and soldier #2's equipment at 3.1 seconds. At time=4 second, Transceiver #1 pings and the ping from Transceiver #1 is received by soldier #1's equipment at 4.55 seconds and soldier #2's equipment at 4.9 seconds. At time=5 second, Transceiver #2 pings and the ping from Transceiver #2 is received by soldier #1's equipment at 5.66 seconds and soldier #2's equipment at 5.1 seconds. At time=6 second, Transceiver #3 pings and the ping from Transceiver #3 is received by soldier #1's equipment at 6.8 seconds and soldier #2's equipment at 6.1 seconds. Note that these time signals are illustrative to teach the pseudo-GPS concept. From this information, the processor computes the pseudo-GPS location and determines that soldier #1 is moving and that soldier #2 is stationary.

FIG. 10 illustrates example regions and associated areas. Note that in the preferred embodiment of this patent, the scanning technique is LIDAR. However, other 3D model generation techniques could be used as well. Other types of imaging that use the electromagnetic spectrum (visible spectrum, infrared spectrum) can be performed. An alternative preferred embodiment is using photogrammetry. Five examples are provided. Example 1 illustrates wherein the region scanned (by LIDAR) is Kabul and the area where the pseudo-GPS system is set up is a warehouse. Example 2 illustrates wherein the region scanned (by LIDAR) is Bagram and the area where the pseudo-GPS system is set up is a a field at Ft. Benning. Example 3 illustrates wherein the region scanned (by LIDAR) is Hyde Park and the area where the pseudo-GPS system is set up is a backyard at a home. Example 4 illustrates wherein the region scanned (by LIDAR) is the Taj Mahal and the area where the pseudo-GPS system is set up is a family room at a home. Example 5 illustrates wherein the region scanned (by LIDAR) is Museum and the area where the pseudo-GPS system is set up is an office at a home. In some embodiments, a scaling factor can be used to allow more rapid exploration of the region as compared to the area. For example, Hyde Park could be scaled down to half size.

Figure 11:
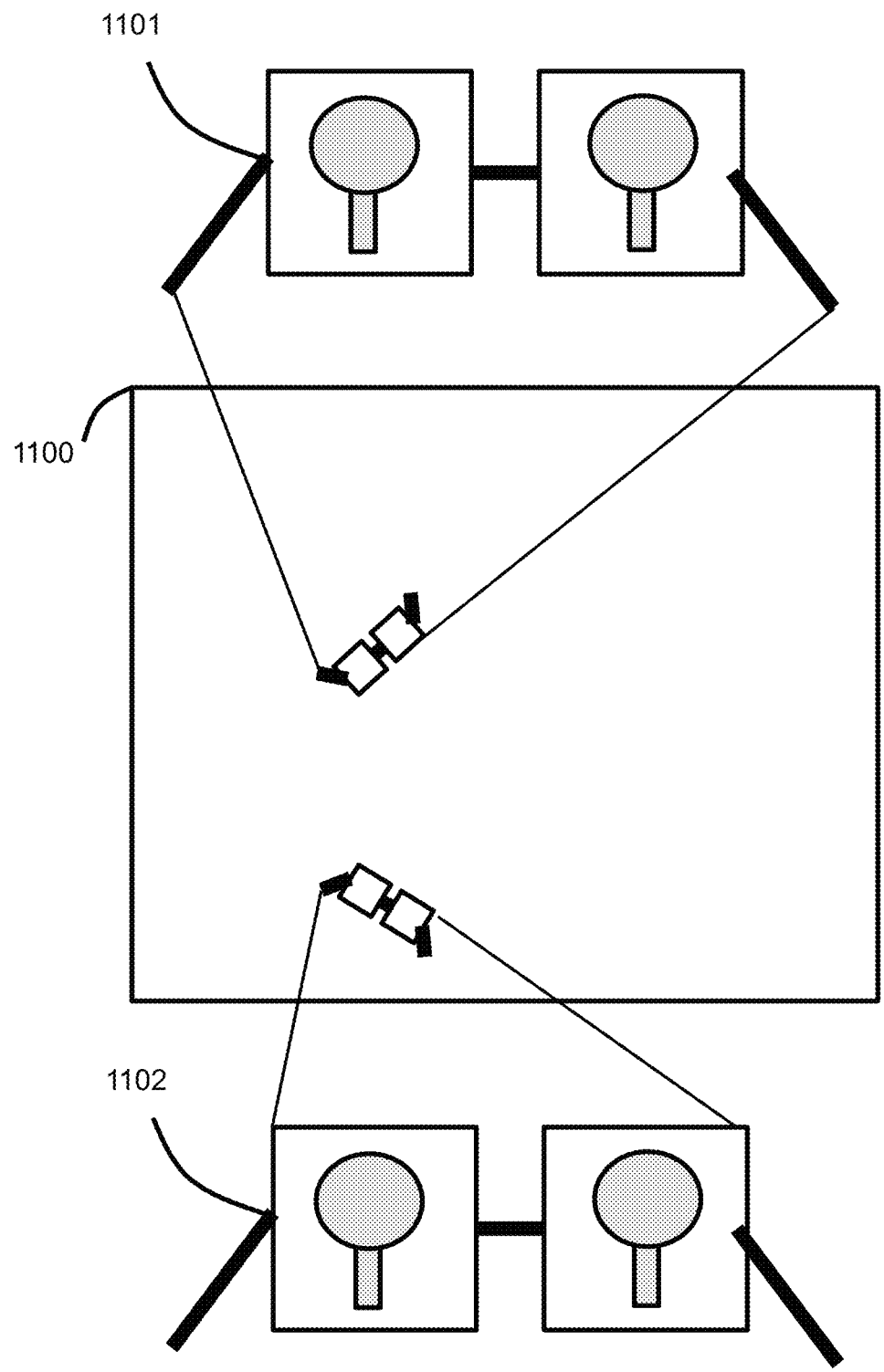
FIG. 11 illustrates an example wherein a first and a second user are in the same area and in the same portion of the region looking at the same object.

FIG. 11 illustrates an example wherein a first and a second user are in the same area and in the same portion of the region looking at the same object. 1100 illustrates the area, which contains the transceivers. Note that in this example, the region is of a field with a tree in Afghanistan. The dataset is a LIDAR scan. 1101 illustrates the first user's glasses, which shows the tree. 1102 illustrates the second user's glasses, which shows the tree.

Figure 12:
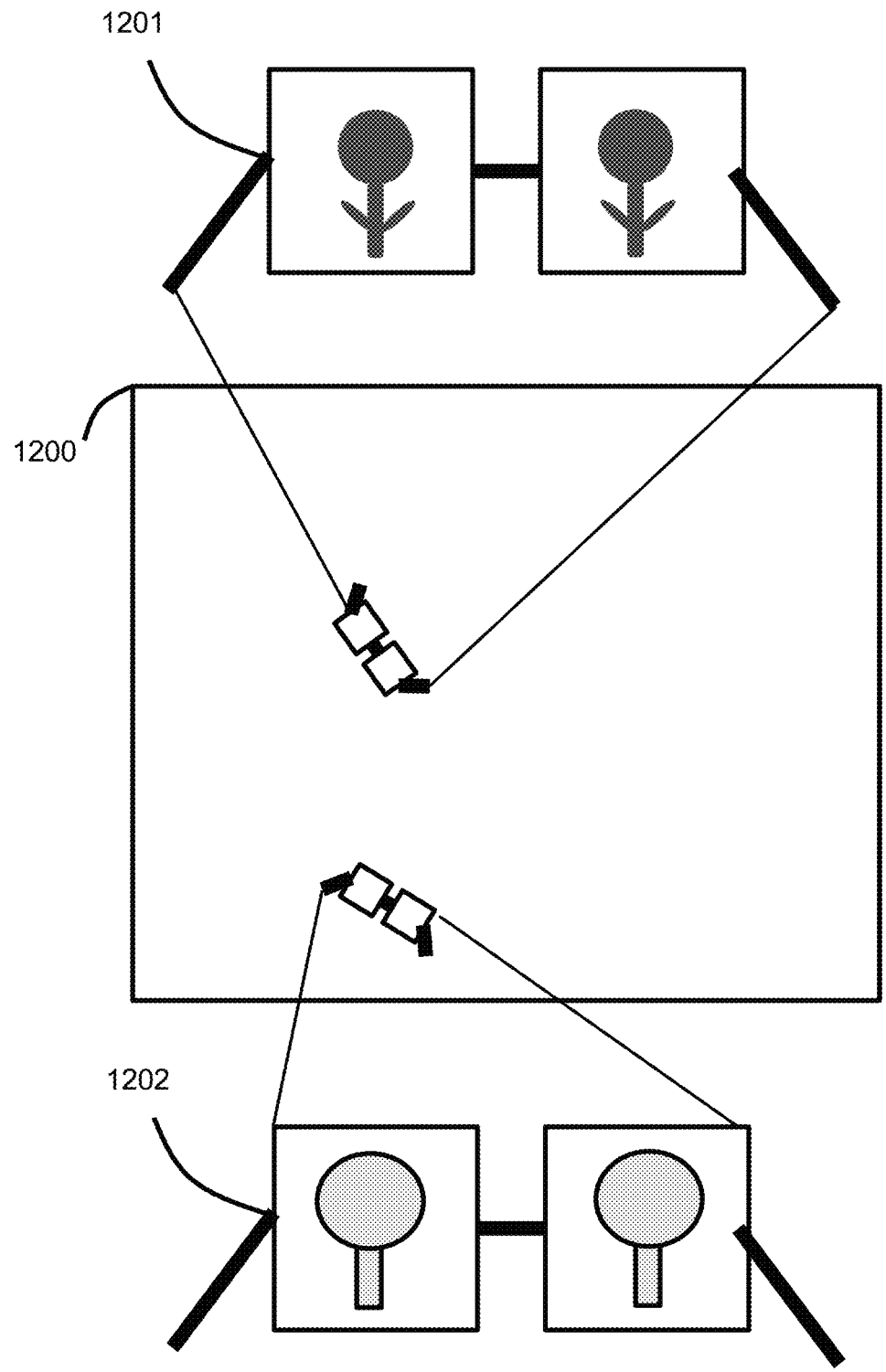
FIG. 12 illustrates an example wherein a first and a second user are in the same area and in the same portion of the region looking at different objects.

FIG. 12 illustrates an example wherein a first and a second user are in the same area and in the same portion of the region looking at different objects. 1200 illustrates the area, which contains the transceivers. Note that in this example, the region is of a field with a tree and a flower in Afghanistan. The dataset is a LIDAR scan. 1201 illustrates the first user's glasses, which shows the flower. 1202 illustrates the second user's glasses, which shows the tree.

Figure 13:
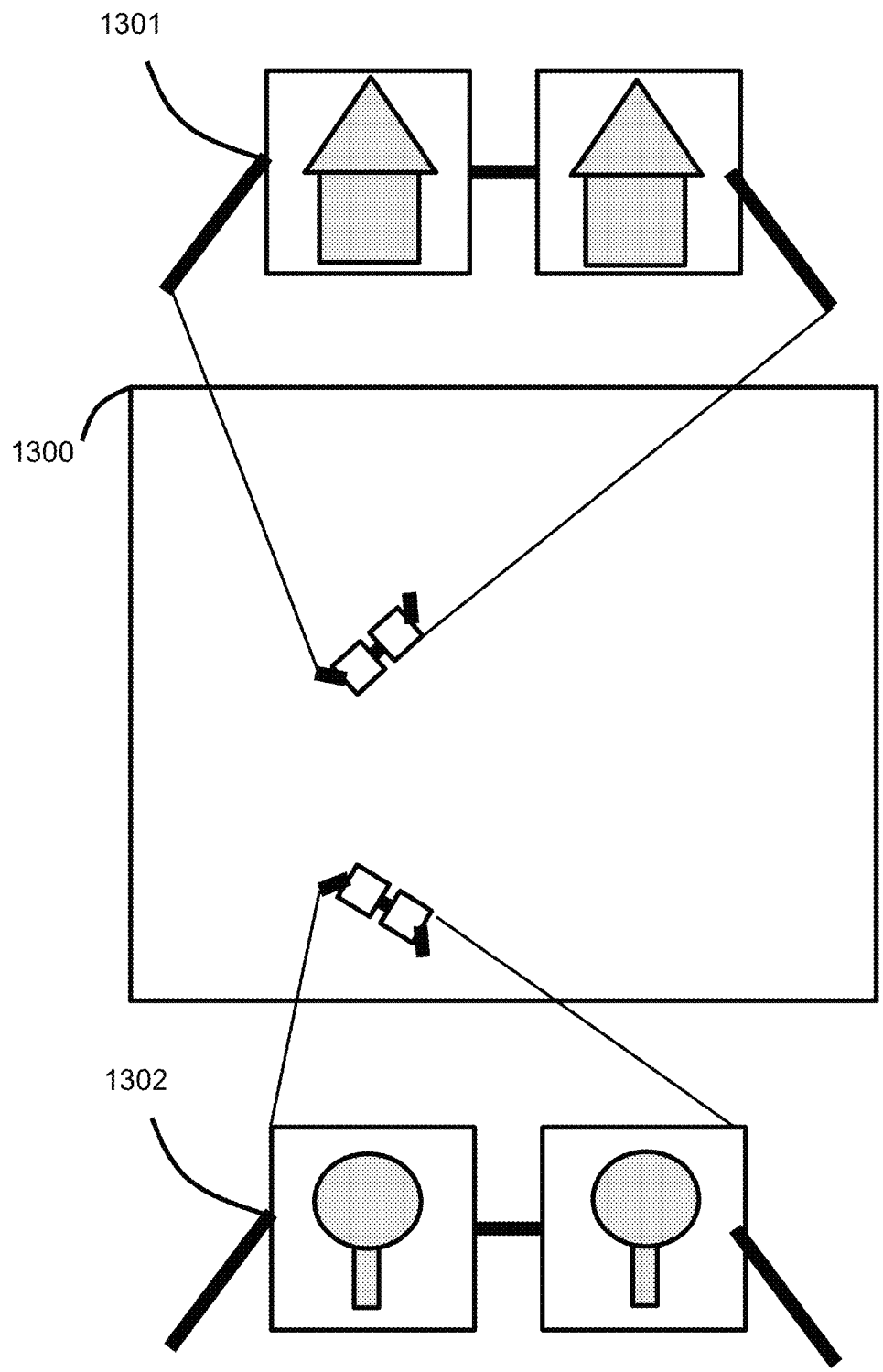
FIG. 13 illustrates an example wherein a first and a second user are in the same area and in the same portion of the region looking at the same object.

FIG. 13 illustrates an example wherein a first and a second user are in the same area and in the same portion of the region looking at the same object. 1300 illustrates the area, which contains the transceivers. Note that in this example, the portion of the region viewed by the first user is of a hut in Afghanistan. Note that in this example, the portion of the region viewed by the second user is of a tree in Afghanistan. The dataset is a LIDAR scan. 1301 illustrates the first user's glasses, which shows a hut. 1302 illustrates the second user's glasses, which shows the tree.

Figure 14:
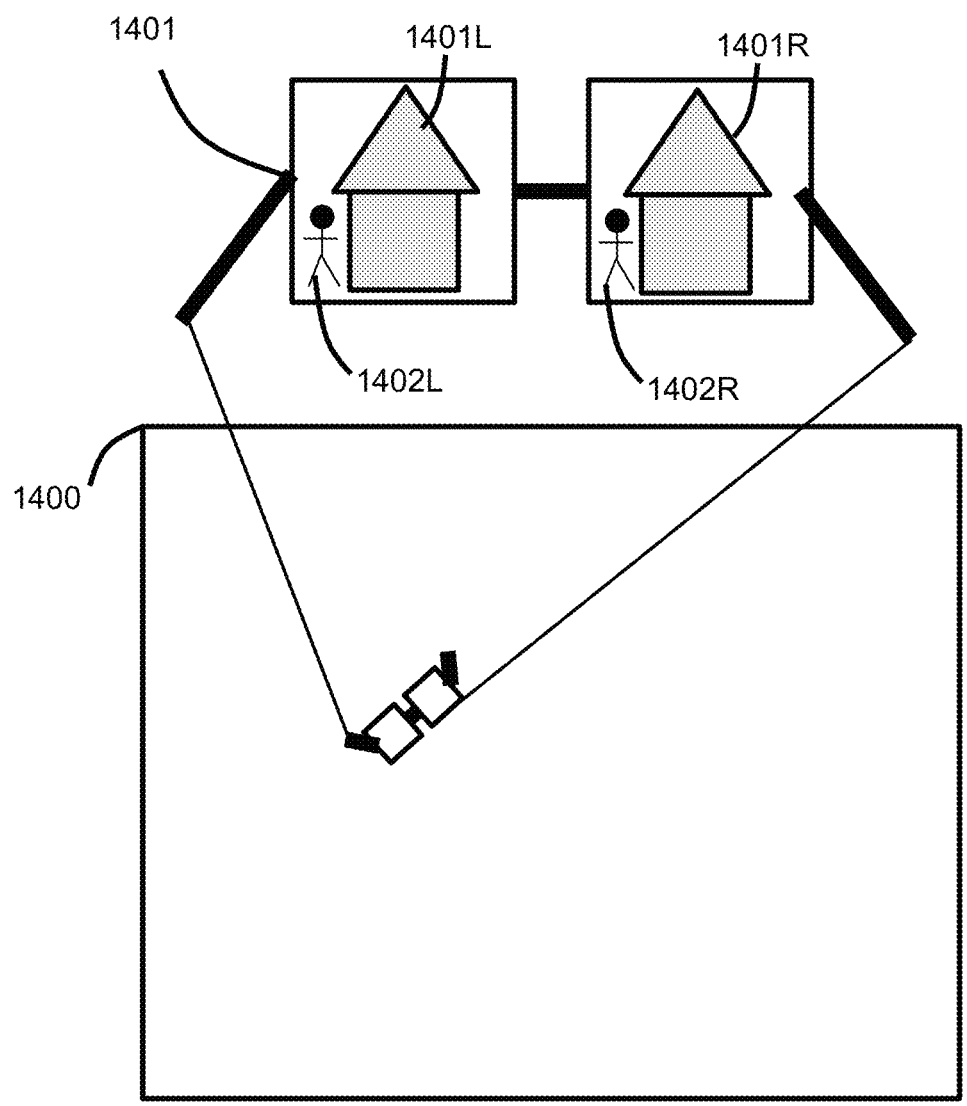
FIG. 14 illustrates inserting additional virtual objects into the scene.

FIG. 14 illustrates inserting additional virtual objects into the scene. In this example, some virtual objects including virtual enemy, virtual tools and virtual terrain features can be displayed on a user's HDU. 1400 illustrates the area, which contains the transceivers. Note that in this example, the portion of the region viewed by the member is of a hut in Afghanistan. The dataset is a LIDAR scan. 1401 illustrates the first user's glasses, which shows a left eye image of a hut 1401L and a right eye image of a hut 1401R. Additionally, this illustrated enhancing the extended reality experience by adding virtual objects to the scene. In this example, a virtual enemy was added to the scene. The left eye image of the virtual enemy 1402L and the right eye image of the virtual enemy 1402L is illustrated as displayed on the first user's augmented reality glasses. Note that is this embodiment, virtual objects not present in the region would be displayed.

Throughout the entirety of the present disclosure, use of the articles "a" or "an" to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. The device(s) or computer systems that integrate with the processor(s) may include, for example, a personal computer (s), workstation(s) (e.g., Sun, HP), personal digital assistant(s) (PDA(s)), handheld device(s) such as cellular telephone(s), laptop(s), handheld computer(s), or another device(s) capable of being integrated with a processor(s) that may operate as provided herein. Accordingly, the devices provided herein are not exhaustive and are provided for illustration and not limitation. References to "a microprocessor and "a processor, or "the microprocessor and "the processor." may be understood to include one or more microprocessors that may communicate in a stand-alone and/or a distributed environment(s), and may thus be configured to communicate via wired or wireless communications with other processors, where such one or more processor may be configured to operate on one or more processor-controlled devices that may be similar or different devices. Use of such "microprocessor or "processor terminology may thus also be understood to include a central processing unit, an arithmetic logic unit, an application-specific integrated circuit (IC), and/or a task engine, with such examples provided for illustration and not limitation. Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where Such memory may be contiguous and/or partitioned based on the application. Accordingly, references to a database may be understood to include one or more memory associations, where such references may include commercially available database products (e.g., SQL, Informix, Oracle) and also include proprietary databases, and may also include other structures for associating memory Such as links, queues, graphs, trees, with such structures provided for illustration and not limitation. References to a network, unless provided otherwise, may include one or more intranets and/or the Internet, as well as a virtual network. References hereinto microprocessor instructions or microprocessor-executable instructions, in accordance with the above, may be understood to include programmable hardware.

Unless otherwise stated, use of the word "substantially' may be construed to include a precise relationship, condition, arrangement, orientation, and/or other characteristic, and deviations thereof as understood by one of ordinary skill in the art, to the extent that such deviations do not materially affect the disclosed methods and systems. Throughout the entirety of the present disclosure, use of the articles "a" or "an' to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, Something else, may be understood to so communicate, be associated with, and or be based on in a direct and/or indirect manner, unless otherwise stipulated herein. Although the methods and systems have been described relative to a specific embodiment thereof, they are not so limited. Obviously many modifications and variations may become apparent in light of the above teachings. Many additional changes in the details, materials, and arrangement of parts, herein described and illustrated, may be made by those skilled in the art. Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed:
1. A method comprising:
using a 3D dataset of a region wherein said 3D dataset is derived from imaging said region;
registering said 3D dataset of said region to an area
  wherein said area is different from said region,
  wherein said area is not superimposed on said region, and
  wherein locations within said area are assigned area coordinates;
using a transceiver system in said area to determine an area coordinate of each augmented reality head display unit (HDU) within said area based on at least:
  an arrival time of a first signal from a first transceiver in said area to each augmented reality HDU;
  an arrival time of a second signal from a second transceiver in said area to each augmented reality HDU; and
  an arrival time of a third signal from a third transceiver in said area to each augmented reality HDU,
determining pseudo-GPS location of said HDU based on:
  said area coordinate of each augmented reality HDU; and
  said registration of said 3D dataset of said region to said area;
performing a simulation for multiple members in said area
  wherein each member wears an augmented reality head display unit (HDU),
  wherein said simulation occurs over multiple time points,
  wherein at a first time point, each member's augmented reality HDU receives initial signal from said transceiver system in said area,
  wherein an initial pseudo-GPS location of each member's augmented reality HDU is computed based on at least:
    said initial signal from said transceiver system in said area which determines an initial area coordinate of each augmented reality HDU; and
    said registration of said 3D dataset of said region to said area,
  wherein an initial image set of said region is generated and displayed on each member's augmented reality HDU based on at least said initial pseudo-GPS location of each member's augmented reality HDU, wherein each member's initial image set comprises a first left eye image and a first right eye image, wherein each member's first left eye image is generated based on at least each member's first left eye viewpoint, each member's first left eye viewing angle and said 3D dataset of said region, wherein each member's first right eye image is generated based on at least each member's first right eye viewpoint, each member's first right eye viewing angle and said 3D dataset of said region, wherein at a subsequent time point, each member's augmented reality HDU receives subsequent signal from said transceiver system in said area, wherein an updated pseudo-GPS location of each member's augmented reality HDU is computed based on at least:

said subsequent signal from said transceiver system in said area which determines a subsequent area coordinate of each augmented reality HDU; and said registration of said 3D dataset of said region to said area, wherein a subsequent image set of said region is generated and displayed on each member's augmented reality HDU based on at least said updated pseudo-GPS location of each member's augmented reality HDU, wherein each member's subsequent image set comprises a subsequent left eye image and a subsequent right eye image, wherein each member's subsequent left eye image is generated based on at least each member's subsequent left eye viewpoint, each member's subsequent left eye viewing angle and said 3D dataset of said region, and wherein each member's subsequent right eye image is generated based on at least each member's subsequent right eye viewpoint, each member's subsequent right eye viewing angle and said 3D dataset of said region.

2. The method of claim 1 further comprising wherein said 3D dataset comprises photogrammetry.

3. The method of claim 2 further comprising wherein a member's HDU displays a location derived from a positioning system of said region.

4. The method of claim 3 further comprising wherein said positioning system comprises at least one of the group of:
a global positioning system (GPS); and
a nominal positioning system (NPS).

5. The method of claim 1 further comprising wherein an element of a member's HDU comprises an inertial measurement unit (IMU) wherein head tracking capabilities are enabled.

6. The method of claim 1 further comprising wherein virtual objects are displayed on a member's HDU.

7. The method of claim 1 further comprising wherein said area comprises one of the group of:
a warehouse;
a room; and
a field.

8. The method of claim 7 further comprising wherein said warehouse area contains a transportation system in communication with a positioning system of said region.

9. The method of claim 1 further comprising wherein said 3D dataset comprises LIDAR.

10. The method of claim 1 further comprising wherein said members comprise a friendly forces group, a neutral forces group and an adversarial forces group.

11. The method of claim 10 further comprising wherein said friendly forces group and said adversarial forces group interact with one another such that virtual damage could be inflicted by the friendly forces group on the adversarial forces group and by the adversarial forces group on the friendly forces group.

12. The method of claim 11 further comprising wherein data from an interaction of said friendly forces group and said adversarial forces group is recorded.

13. The method of claim 12 further comprising wherein said recorded data can be summarized for subsequent analysis or education purposes.

14. The method of claim 10 further comprising wherein a virtual adversarial group is presented on HDU's of said friendly forces group.

15. The method of claim 1 further comprising wherein members carry equipment that can also be located via the transceiver system.

16. The method of claim 1 further comprising:
wherein at least one additional user wearing HDU(s) is located in at least one additional area and views 3D imagery of said region; and
wherein said at least one additional area is different from said area.

17. The method of claim 1 further comprising wherein said region is the same as said area.

18. A set of augmented reality head display units (HDUs) configured to be worn on members' heads comprising:
wherein each augmented reality head display unit comprises:
a left eye display;
a right eye display;
a processor;
an inertial measurement unit (IMU); and
a communications system;
wherein said set of augmented reality head display units uses a 3D dataset of a region;
wherein said 3D dataset of said region is registered to an area
wherein said area is different from said region,
wherein said area is not superimposed on said region, and
wherein locations within said area are assigned area coordinates;
wherein said set of augmented reality HDUs works in conjunction with a transceiver system in said area to determine an area coordinate of each augmented reality head display unit (HDU) of said set of augmented reality HDUs within said area based on at least:
an arrival time of a first signal from a first transceiver in said area to each augmented reality HDU,
an arrival time of a second signal from a second transceiver in said area to each augmented reality HDU; and
an arrival time of a third signal from a third transceiver in said area to each augmented reality HDU;
determining a pseudo-GPS location of said HDU based on;
said area coordinate of said each augmented reality HDU; and
said registration of said 3D dataset of said region to said area; and
wherein said set of augmented reality HDUs aids in a simulation for multiple members in said area
wherein each member wears an augmented reality HDU, wherein said simulation occurs over multiple time points,
wherein at a first time point, each member's augmented reality HDU receives initial signal from said transceiver system in said area,
wherein an initial pseudo-GPS location of each member's augmented reality HDU is computed based on at least:
  said initial signal from said transceiver system in said area which determines an initial area coordinate of each augmented reality HDU; and
  said registration of said 3D dataset of said region to said area,
wherein an initial image set of said region is generated and displayed on each member's augmented reality HDU based on at least said initial pseudo-GPS location of each member's augmented reality HDU,
wherein each member's initial image set comprises a first left eye image and a first right eye image,
wherein each member's first left eye image is generated based on at least each member's first left eye viewpoint, each member's first left eye viewing angle and said 3D dataset of said region,
wherein each member's first right eye image is generated based on at least each member's first right eye viewpoint, each member's first right eye viewing angle and said 3D dataset of said region,
wherein at a subsequent time point, each member's augmented reality HDU receives subsequent signal from said transceiver system in said area,
wherein an updated pseudo-GPS location of each member's augmented reality HDU is computed based on at least:
  said subsequent signal from said transceiver system in said area which determines a subsequent area coordinate of each augmented reality HDU; and
  said registration of said 3D dataset of said region to said area,
wherein a subsequent image set of said region is generated and displayed on each member's augmented reality HDU based on at least said updated pseudo-GPS location of each member's augmented reality HDU,
wherein each member's subsequent image set comprises a subsequent left eye image and a subsequent right eye image,
wherein each member's subsequent left eye image is generated based on at least each member's subsequent left eye viewpoint, each member's subsequent left eye viewing angle and said 3D dataset of said region, and
wherein each member's subsequent right eye image is generated based on at least each member's subsequent right eye viewpoint, each member's subsequent right eye viewing angle and said 3D dataset of said region.

19. A system for simulating activities in a warehouse comprising:
a warehouse where members wearing a set of augmented reality head display units (HDUs) can maneuver; and
a transceiver system located in said warehouse
  wherein said set of augmented reality HDUs use a 3D dataset of a region,
  wherein said 3D dataset of said region is registered to said warehouse,
  wherein said warehouse is not within said region,
  wherein locations within said warehouse are assigned warehouse coordinates,
  wherein said set of augmented reality HDUs works in conjunction with said transceiver system located in said warehouse to determine a warehouse coordinate of each augmented reality HDU of said set of augmented reality HDUs within said warehouse based on at least:
    an arrival time of a first signal from a first transceiver in said warehouse to each augmented reality HDU;
    an arrival time of a second signal from a second transceiver in said warehouse to each augmented reality HDU; and
    an arrival time of a third signal from a third transceiver in said warehouse to each augmented reality HDU;
  wherein said set of augmented reality HDUs aids in a simulation for said members,
  wherein each member wears an augmented reality HDU,
  wherein said simulation occurs over multiple time points,
  wherein at a first time point, each member's augmented reality HDU receives initial signal from said transceiver system in said warehouse,
  wherein an initial pseudo-GPS location of each member's augmented reality HDU is computed based on at least:
    said initial signal from said transceiver system in said warehouse which determines an initial warehouse coordinates of each augmented reality HDU; and
    said registration of said 3D dataset of said region to said warehouse,
  wherein an initial image set of said region is generated and displayed on each member's augmented reality HDU based on at least said initial pseudo-GPS location of each member's augmented reality HDU,
  wherein each member's initial image set comprises a first left eye image and a first right eye image,
  wherein each member's first left eye image is generated based on at least each member's first left eye viewpoint, each member's first left eye viewing angle and said 3D dataset of said region,
  wherein each member's first right eye image is generated based on at least each member's first right eye viewpoint, each member's first right eye viewing angle and said 3D dataset of said region,
  wherein at a subsequent time point, each member's augmented reality HDU receives subsequent signal from said transceiver system in said warehouse,
  wherein an updated pseudo-GPS location of each member's augmented reality HDU is computed based on at least:
    said subsequent signal from said transceiver system in said warehouse which determines a subsequent warehouse coordinate of each augmented reality HDU; and
    said registration of said 3D dataset of said region to said warehouse,
  wherein a subsequent image set of said region is generated and displayed on each member's augmented reality HDU based on at least said updated pseudo-GPS location of each member's augmented reality HDU, wherein each member's subsequent image set comprises a subsequent left eye image and a subsequent right eye image, wherein each member's subsequent left eye image is generated based on at least each member's subsequent left eye viewpoint, each member's subsequent left eye viewing angle and said 3D dataset of said region, and wherein each member's subsequent right eye image is generated based on at least each member's subsequent right eye viewpoint, each member's subsequent right eye viewing angle and said 3D dataset of said region.

* * * * *